United States Patent
Snyder

Patent Number: 5,394,084
Date of Patent: Feb. 28, 1995

[54] METHOD AND APPARATUS FOR REDUCING ERRORS IN EDDY-CURRENT CONDUCTIVITY MEASUREMENTS DUE TO LIFT-OFF BY INTERPOLATING BETWEEN A PLURALITY OF REFERENCE CONDUCTIVITY MEASUREMENTS

[75] Inventor: Patrick J. Snyder, Seattle, Wash.

[73] Assignee: The Boeing Company, Seattle, Wash.

[21] Appl. No.: 47,163

[22] Filed: Apr. 14, 1993

Related U.S. Application Data

[63] Continuation of Ser. No. 814,363, Dec. 23, 1991, abandoned.

[51] Int. Cl.⁶ .................. G01N 27/02; G01N 27/90; G01R 33/12; G01R 35/00
[52] U.S. Cl. ..................... 324/225; 324/233; 324/236; 324/202; 324/656; 324/712
[58] Field of Search ............... 324/202, 207, 12, 225, 324/226, 236–242, 233, 712, 653–656, 445

[56] References Cited

U.S. PATENT DOCUMENTS

| | | | |
|---|---|---|---|
| 3,358,225 | 12/1967 | Peugeot | 324/225 |
| 3,449,661 | 6/1969 | Puidak | 324/225 |
| 3,755,096 | 8/1973 | Wiers | 324/233 |
| 3,936,734 | 2/1976 | Brandli et al. | 324/225 |
| 4,000,458 | 12/1976 | Miller et al. | 324/236 |
| 4,006,405 | 2/1977 | Greenwood et al. | 324/227 |
| 4,074,186 | 2/1978 | Flaherty | 324/222 |
| 4,095,180 | 6/1978 | Brown | 324/233 |
| 4,126,491 | 11/1978 | Karlsson | 324/240 X |
| 4,210,866 | 7/1980 | Paulson | 324/225 |
| 4,351,031 | 9/1982 | Flaherty et al. | 364/580 |
| 4,450,405 | 5/1984 | Howard | 324/234 |
| 4,553,094 | 11/1985 | Gehrke | 324/225 |
| 4,556,846 | 12/1985 | D'Hondt | 324/238 |
| 4,564,810 | 1/1986 | Geithman et al. | 324/230 |
| 4,609,870 | 9/1986 | Lale et al. | 324/225 |
| 4,620,152 | 10/1986 | Bains, Jr. | 324/225 |
| 4,673,877 | 6/1987 | Sakamoto et al. | 324/225 |
| 4,727,322 | 2/1988 | Lonchampt et al. | 324/225 |
| 4,821,204 | 4/1989 | Huschelrath | 364/481 |
| 4,922,201 | 5/1990 | Vernon et al. | 324/225 X |
| 4,924,182 | 5/1990 | Vernon et al. | 324/225 X |
| 4,942,545 | 7/1990 | Sapia | 364/571.01 |
| 4,963,826 | 10/1990 | Capobianco et al. | 324/202 |
| 5,130,651 | 7/1992 | Morrey, Jr. | 324/225 |

FOREIGN PATENT DOCUMENTS 1376035  2/1988  U.S.S.R. ............... 324/202

*Primary Examiner*—Gerard R. Strecker
*Assistant Examiner*—Warren S. Edmonds
*Attorney, Agent, or Firm*—Christensen, O'Connor, Johnson & Kindness

[57] ABSTRACT

An eddy-current apparatus for measuring the conductivity of a conductive material and for reducing the influence of lift-off on conductivity measurements is provided. The apparatus includes a probe for inducing an eddy-current in a conductive material and a digital LCR meter for measuring the impedance of the probe when it is placed near the conductive material. A digital processor uses calibration impedance data obtained from a series of reference materials and an impedance measurement for a test material to produce a conductivity value independent of lift-off between the probe and the test material.

12 Claims, 4 Drawing Sheets

METHOD AND APPARATUS FOR REDUCING ERRORS IN EDDY-CURRENT CONDUCTIVITY MEASUREMENTS DUE TO LIFT-OFF BY INTERPOLATING BETWEEN A PLURALITY OF REFERENCE CONDUCTIVITY MEASUREMENTS

This application is a continuation application based on prior application Ser. No. 07/814,363, filed on Dec. 23, 1991, now abandoned.

FIELD OF THE INVENTION

The present invention relates to test equipment for measuring conductivity using an electromagnetic induction or eddy-current method.

BACKGROUND OF THE INVENTION

Eddy-current methods for non-destructive inspection are widely used in industry. Eddy-current methods can be used to measure the conductivity of conductive parts, as well as to detect cracks or flaws in such parts. A common application for the eddy-current method is to measure the conductivity of metal parts in order to ensure quality control. Eddy-current methods are particularly useful in the quality control of parts made of alloys, such as those of aluminum, in which deviations in the conductivity of the part indicates an improper mixture of alloyed metals, and/or incorrect heat treatment. Conductivity can also be used to determine the grade or temper of the alloy. Eddy-current conductivity testing is widely used in the manufacturing of aircraft components due to the widespread use of aluminum alloys.

In general, eddy-current testing works according to the following principle. An electrical coil is placed on the surface of a conductive material on which properties are to be measured. The coil is then excited using an alternating current. This produces an alternating magnetic field surrounding the coil that induces a circulating current or "eddy-current" in the material. In turn, the induced eddy-current induces a secondary voltage in the coil. The net effect of this secondary voltage is to change the impedance of the coil. The induced eddy-current, and thus the secondary voltage, is a function of the conductivity of the material.

Conductivity of non-ferrous metals is commonly specified as a percentage compared to copper. This unit is known as "%IACS" which stands for "Percent International Annealed Copper Standard." This standard is a hypothetical copper bar 1 m×1 mm×1 mm having a resistance of 1/58 ohm. Typically, eddy-current equipment is calibrated by detecting the impedance of the probe coil as the probe is applied to materials of known %IACS ("reference materials"). Any subsequent test material which produces an impedance in the probe similar to that caused by one of the known materials is assumed to have the same conductivity.

One of the major causes of error in conductivity measurements using the eddy-current method is known as "lift-off." Lift-off is the spacing between the electrical coil used to measure conductivity and the conductive material upon which measurements are to be taken. Lift-off can be caused by surface roughness, surface curvature, or a number of other factors which prevent the measuring coil from properly contacting the test material. The accuracy of the conductivity measurements can be increased by maintaining the probe and the conductive materials in a temperature-controlled oil bath prior to and during the conductivity measurements. This procedure maintains the probe and the conductive materials at a constant temperature, thus reducing any measurement errors due to temperature variations. However, the oil forms a film, that can vary in thickness, between the probe and the conductive materials. This thickness variation can also produce lift-off between the probe and the conductive materials.

Lift-off changes both the magnitude and phase of the impedance of the electrical coil used to measure the conductivity. This is important because some prior art methods use the magnitude of the impedance as an indication of conductivity while other methods use the phase of the impedance. In either case, lift-off results in an error in the subsequent observed value of conductivity associated with the measured impedance.

Some eddy-current systems use a balanced-bridge technique for making conductivity measurements. An electrical coil used to measure conductivity is connected in one arm of an electrical bridge. A variable resistor and/or capacitor are connected in the other arms of the bridge. The variable resistor and/or capacitor are used to balance the bridge and indicate the change in impedance. This method is capable of good accuracy, but is very time consuming to use. It is possible to reduce the effects of lift-off by adding an additional variable capacitor into the bridge circuit. This capacitor is adjusted, while the probe is placed on a typical conductive material, so as to make the bridge balance insensitive to lift-off. However, the adjustment is most effective only for materials whose conductivity is close to the conductivity of the material on which the adjustment was made. For other materials, the adjustment is only partially effective and the sensitivity of the system to lift-off is reduced but not eliminated. Therefore, in order to ensure that the effects of lift-off are eliminated, the bridge must be readjusted when a material whose conductivity is outside a limited range of conductivity is tested. Furthermore, inaccurate results are obtained if the adjustment is not done properly.

Other eddy-current systems use a digital inductance-capacitance-resistance (LCR) meter with high accuracy to measure the impedance of the electrical coil. The digital LCR meter is connected to a computer through an electrical interface. These systems rely on careful probe placement to minimize lift-off.

Thus, a number of methods have been devised to try and reduce the effects of lift-off. These methods are capable of achieving accurate results; however, the methods are complex and an operator that is unskilled or inattentive often fails to achieve accurate measurements. As a result, defective parts pass through inspection without being detected.

SUMMARY OF THE INVENTION

The eddy-current apparatus and method of the present invention reduces the influence of lift-off on conductivity measurements, thus increasing accuracy. It does so without the time consuming and complex steps associated with prior art methods.

In an embodiment of the method and apparatus of the present invention, probe means for inducing an eddy-current in a conductive material and detecting means for detecting the resulting impedance of the probe means are provided. A digital processing means comprising calibration means and measurement means is also provided. The calibration means uses the probe means and detecting means to produce calibration data comprising at least two conductivity measurements for each of a plurality of reference materials. The measurement means uses the probe means and detecting means to make a conductivity measurement for the test material and adjusts this measurement using the calibration data in order to reduce its dependence upon the lift-off of the probe means.

According to other aspects of the invention, the measurement means includes means for adjusting the conductivity measurement for the test material for both a phase change and an amplitude change caused by lift-off. The apparatus also includes means for calculating a quantity representative of the effects of liftoff on a selected value of conductivity. The quantity used is the rate of change of the reactance with respect to a change in resistance. The measurement means further includes means for determining the difference between the selected value of conductivity and the conductivity measurement for the test material and means for iteratively adjusting the selected value of conductivity until the difference is less than a tolerance value.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings.

DETAILED DESCRIPTION OF THE PREFERRED EMBODIMENT

The present invention provides a highly accurate and easily automated procedure for measuring conductivity. The invention eliminates the complex and error prone steps used in the prior art while increasing the accuracy of conductivity measurements over the prior art.

Figure 1:
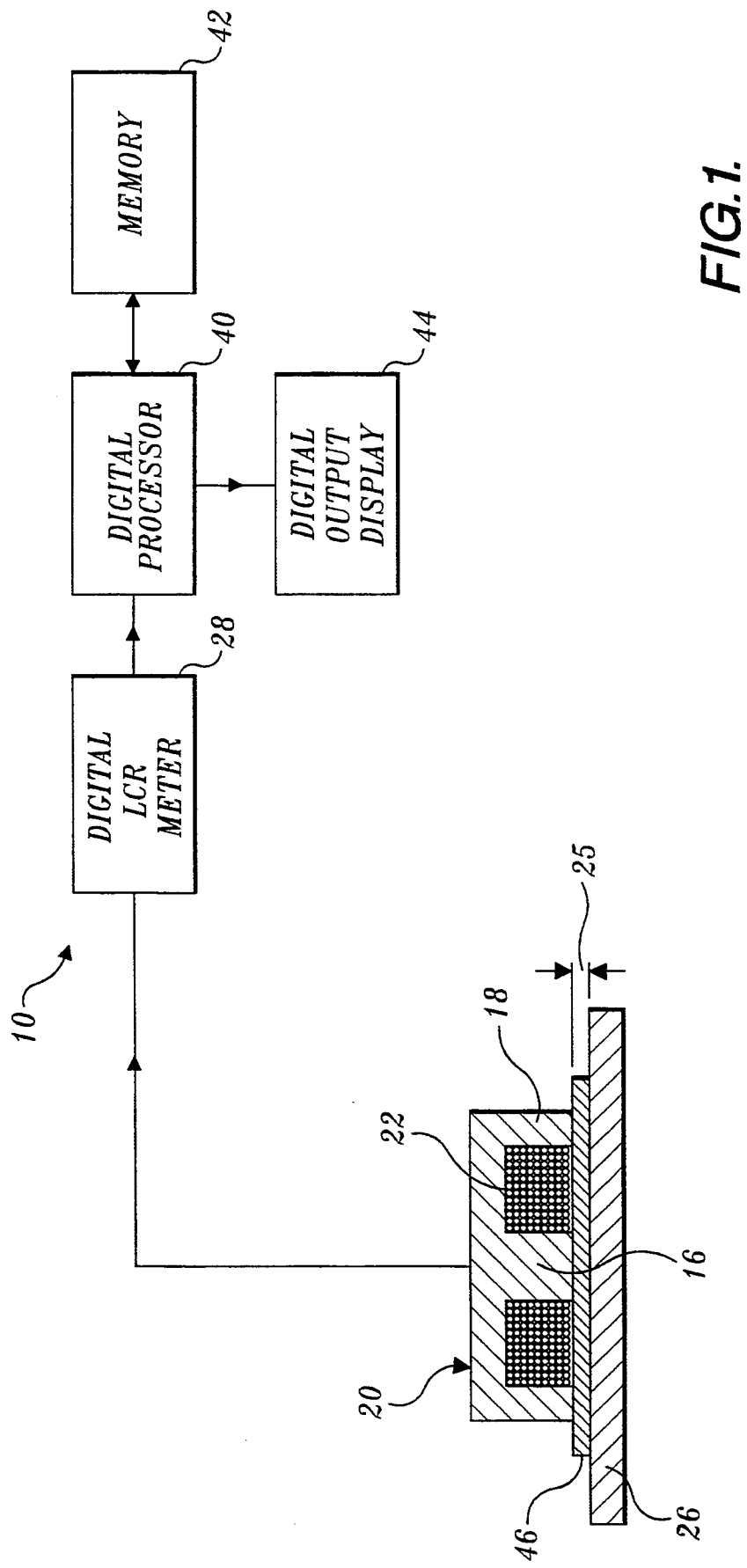
FIG. 1 is a schematic of an apparatus for measuring electrical conductivity by the eddy-current method of the present invention.

FIG. 1 shows a schematic of an eddy-current conductivity measurement apparatus 10 according to the present invention. Apparatus 10 includes an electrical probe 20 that has a case 18 formed of a ferromagnetic material, such as a ferrite compound. In the preferred embodiment, the case 18 is cylindrical and has a central, downwardly projecting arm 16. The case 18 forms a doughnut-shaped cavity around the arm 16. This cavity is filled with one or more turns of electrical windings 22 that wind around the arm 16. The windings 22 are formed of a highly conductive material, such as copper wire.

The probe 20 is electrically connected to a digital LCR meter 28. The meter 28 serves a two-fold function. First, it supplies an AC current to the probe 20 which causes the windings 22 to produce an alternating magnetic field. This magnetic field passes through the case 18 and impinges upon a conductive material 26 positioned near the probe. This alternating magnetic field, in turn, induces a circulating electric current or "eddy-current" (not shown) in the conductive material 26. This eddy-current influences the probe 20 by changing the impedance of the windings 22.

In the preferred embodiment, the case 18 serves to focus the magnetic field onto the conductive material 26, thus increasing the sensitivity of the apparatus 10. It is desirable to use the case 18 to increase the sensitivity of the apparatus; however, the apparatus will work with a simple coil 22.

The LCR meter 28 also measures the impedance of the probe 20. Impedance is defined as the ratio and phase relationship between the AC current drawn by the coil 22 and the voltage applied to the coil. The LCR meter measures these two quantities, as well as their phase relationship in order to calculate the impedance of the probe. Impedance is conventionally described as consisting of a resistive value (R) and a reactive value (X). Impedance can also be described as an absolute magnitude and a phase value.

In the preferred embodiment, the LCR meter produces a digital signal comprising either a resistance (R) and a reactance (X) or an absolute magnitude and a phase which is received by a digital processor 40. The processor 40 may be any type of processing device such as a microprocessor, microcontroller, or CPU. The processor 40 includes a memory 42 and a digital output display 44 connected to it.

Figure 2:
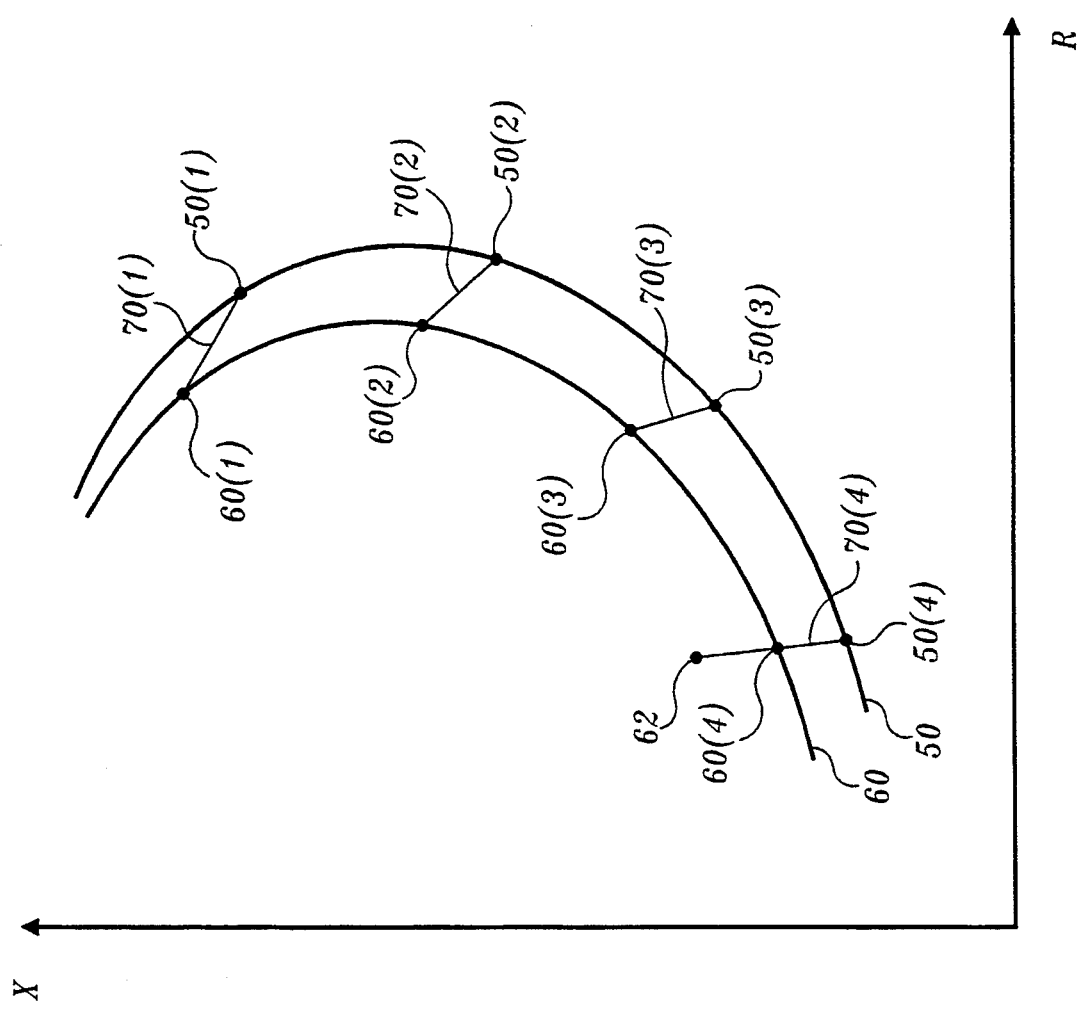
FIG. 2 is a graph showing the errors in conductivity measurement caused by lift-off, the resistance represents the x-axis while reactance represents the y-axis.

FIG. 2 is a graph showing the values of impedance measured in the windings 22 when the probe 20 is placed near a series of conductive materials. For purposes of explanation, the impedance values are represented as points on a plane. For each impedance value, the value of resistance (R) is plotted on the horizontal or x-axis while the value of reactance (X) is plotted on the vertical or y-axis. When the values of impedance measured for materials of varying conductivity are plotted, they define a curve 50 (FIG. 2). The curve 50 is defined by a series of impedance values 50(1-4) measured for four different materials of known conductivity. To measure the values 50(1-4), the probe 20 is placed directly on the surface of each material and the impedance values are measured by the LCR meter 28. That is, the values 50 are measured with minimal lift-off between the probe 20 and the test material 26.

The curve 60 is defined by a series of measurements taken upon the same materials above after an amount of separation or "lift-off" 25 (FIG. 1) has been introduced between the probe 20 and the material 26. The "lift-off" may be introduced by placing a shim 46 between the material 26 and the probe 20. As shown in FIG. 2, as lift-off is introduced between the material 26 and the probe 20, different values of impedance are measured. A small amount of lift-off can result in a significant change in the measured impedance. A set amount of lift-off causes the conductivity curve 50 to move to the inner curve 60.

Lift-off shifts the value of impedance measured for each material in a direction at least partially normal to curve 50 (FIG. 2), while changes in conductivity shift the value of impedance measured along the curve 50. Therefore, it is possible to isolate the effects of lift-off from the effects of conductivity changes. This fact is essential to the operation of both the present invention and prior art methods of compensating for lift-off.

As an example, using the fourth material corresponding to values 50(4) and 60(4), a larger amount of lift-off can be introduced between the material and the probe. This causes a further shift in the measured impedance, resulting in a measured impedance value 62. For a given value of conductivity, lift-off shifts the impedance along a single direction. Thus, differing amounts of lift-off shift the measured value of impedance along a line 70(4) passing through values 62, 60(4), and 50(4). Therefore, the line 70(4) represents the influence of lift-off on the impedance measured for the fourth material. Similarly, the line 70(3) defined by the values 50(3) and 60(3) represents the influence of lift-off on the value of impedance measured for the third material.

Each line 70 corresponds to a certain value of conductivity, and each value of conductivity may be represented by such a line. Therefore, the lines 70 may be thought of as lines of constant conductivity. While the position of individual impedance values measured are affected by lift-off, the position of the lines 70 are not. Varying amounts of lift-off slides the measured value of impedance along one of the lines 70, but does not move the measured value of impedance off the line itself. Note, that it is not necessary to achieve zero lift-off to define a line 70 that corresponds to a given value of conductivity. It is only necessary to determine two values of impedance measured with different amounts of lift-off. This principle allows the influence of lift-off on an observed value of conductivity to be reduced as described below.

Figure 3:
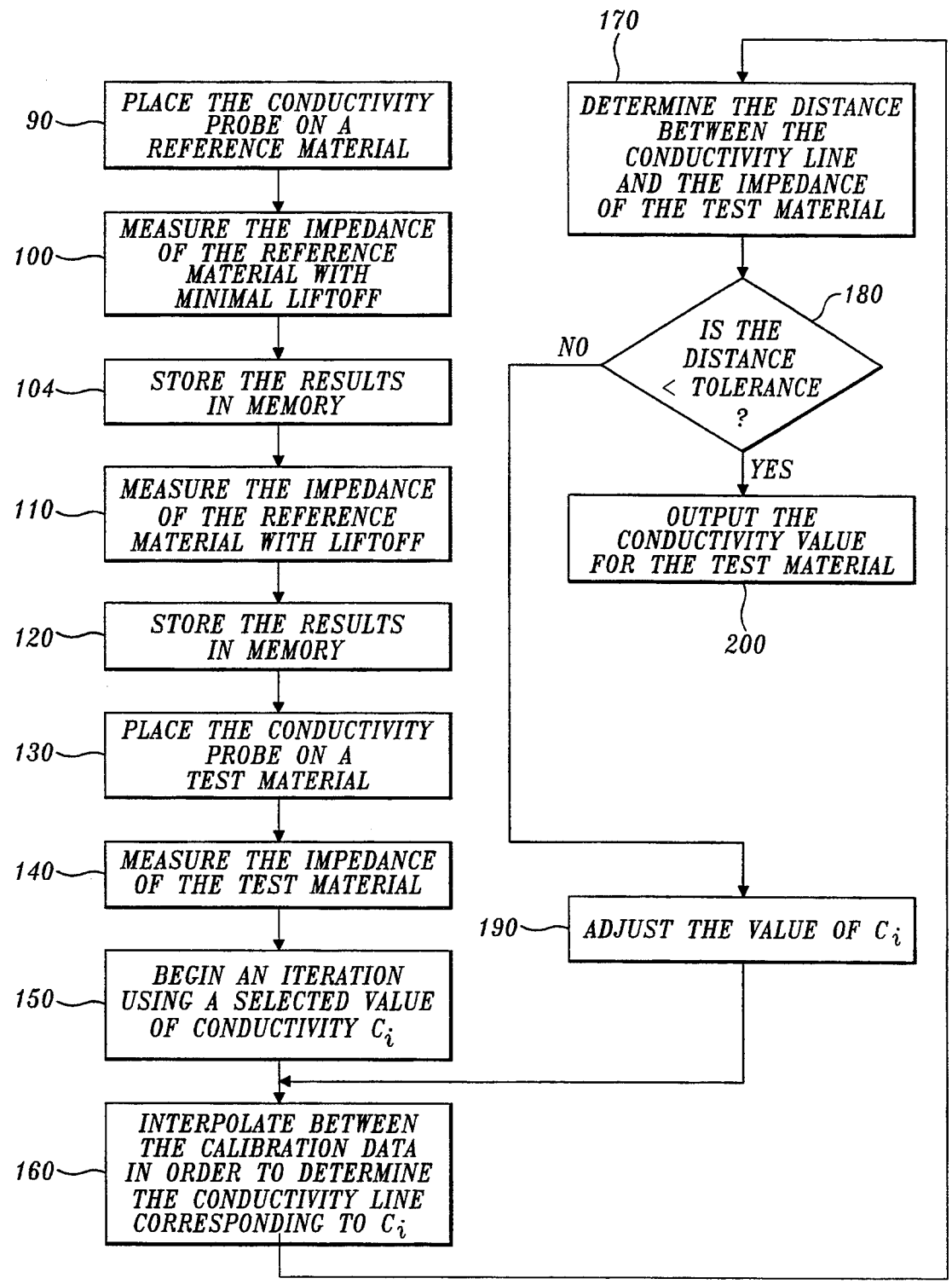
FIG. 3 is a flow chart showing the preferred steps of the eddy-current method of the present invention.
Figure 4:
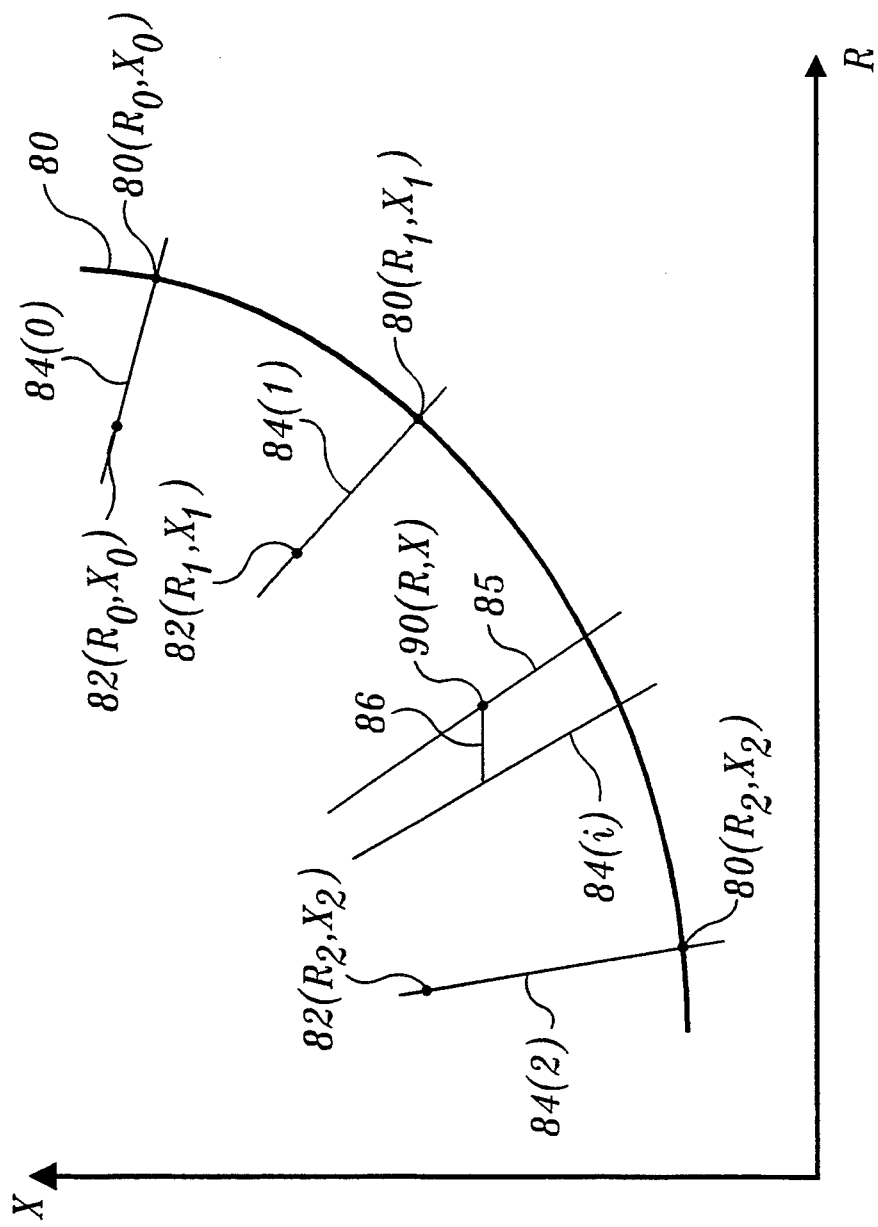
FIG. 4 is a graph showing an application of the steps of FIG. 3.

FIG. 3 shows the steps used in the preferred embodiment to reduce the influence of lift-off on conductivity measurements. The conductivity probe 20 is placed directly upon a reference material of known conductivity such that there is minimal lift-off present between the probe and the reference material as shown in step 90. The LCR meter 28 then detects the impedance of the windings 22, and passes the results to the processor 40 as shown in step 100. In step 104, the processor 40 stores the measured impedance and a corresponding value of conductivity for each reference material in the memory 42. As an example, FIG. 4 shows three values $80(R_0, X_0)$, $80(R_1, X_1)$ and $80(R_2, X_2)$ of impedance measured for three reference materials. Each value 80 has a resistance value (R) and a reactance value (X).

In step 110, the impedances for the same reference materials used above are measured with a predetermined degree of lift-off. In these measurements, a non-conductive shim 46 (FIG. 1) is placed between the probe 20 and the reference material. In the preferred embodiment, a plastic shim 0.5 mm thick is used; however, shims ranging between 0.25–5 mm should produce acceptable results. The shim thickness should be kept below a threshold value at which point the influence of lift-off becomes significantly nonlinear.

The measured values of impedance are recorded by the processor 40 and stored in the memory 42 as indicated in Step 120. The values $82(R_0, X_0)$, $82(R_1, X_1)$ and $82(R_2, X_2)$ (FIG. 4) correspond to the impedances measured after a reference amount of lift-off is introduced between the probe and each reference material. Steps 90–120 are repeated for a series of reference materials with conductivity values ranging over the values of the materials which will be standardly tested with the apparatus 10.

In the preferred embodiment, steps 90–120 are performed prior to using the apparatus 10 to measure the conductivity of test materials. These steps constitute the steps used to calibrate the apparatus and should be performed periodically to allow for wear and drift in the characteristics of the apparatus, but need not be performed prior to each measurement.

In order to measure the conductivity of a test material, the probe 20 is placed on the surface of the test material as indicated in step 130. In the present invention, it is only necessary for the meter 28 to measure a single impedance value 90(R, X) (FIG. 4) as shown in step 140. This value is then passed in the form of a digital signal to the processor 40. The processor then calculates the value of conductivity for the test material independent of the lift-off, as described below.

In order to determine the conductivity of the test material, the processor determines the constant conductivity line 85 that passes (to within practical accuracy) through the measured impedance value 90(R, X). The fact that the conductivity line 85 passes through the impedance 90(R, X) means that it corresponds to the conductivity of the test material, as described above. As noted above, since the position of the constant conductivity lines are independent of lift-off, the value of conductivity thus determined will be independent of the effects of lift-off.

The position of the conductivity line 85 and the corresponding conductivity value are determined through the use of an iterative numerical technique. The processor 40 uses the values 80 and the values 82 measured during the calibration phase in order to calculate the conductivity lines 84(0–2). As an example, line 84(2) is described numerically within the processor as a line which passes through value $80(R_2, X_2)$ and has a slope M2. The slope M2 is calculated as the ratio between the difference in resistance X and reactance R, in other words, the slope between the values $82(R_2, X_2)$ and $80(R_2, X_2)$. Therefore, the conductivity line 84(2) has four parameters associated with it, the conductivity value $C_2$, the R and X values of value $80(R_2, X_2)$ and the slope M2. Each of the conductivity lines 84(0–1) is similarly defined. The conductivity of the test material for which the impedance value 90(R, X) was measured is produced by determining the comparable parameters that define the conductivity line 85.

In step 150, the processor selects a conductivity value $C_i$ and begins an iteration. The conductivity value $C_i$ on which the iteration begins can be any value of conductivity, which will allow the interpolation routine used to converge. The preferred embodiment begins the iteration using a value of conductivity which falls between the values of conductivity corresponding to the conductivity lines which bracket the measured value 90(R, X), in the example shown lines 84(1) and 84(2). Specifically, the preferred embodiment averages the conductivity values which correspond to lines 84(1) and 84(2) in order to produce $C_i$.

The processor then interpolates using the conductivity lines 84 measured for the reference materials in order to determine a conductivity line 84(i) which corresponds to the conductivity value $C_i$. After determining the conductivity line 84(i), the processor determines the distance 86 by which the conductivity line 84(i) misses the value 90(R, X) and notes whether the conductivity line 84(i) falls to the left or right of the value as indicated in step 170. In the preferred embodiment, the distance 86 is the difference between the value of resistance R for the measured impedance value 90(R, X) and the value of resistance R for the conductivity line 84(i) at the value of reactance X for the measured impedance value 90(R, X).

In step 180, if the distance 86 is not within an acceptable tolerance, typically the accuracy limit of the processor, the processor continues to step 190. In step 190, the processor selects a new conductivity value $C_i$ and calculates a corresponding conductivity line 84(i). The new value of conductivity $C_i$ is selected such that the corresponding conductivity line 84(i) is closer to the value 90(R, X) than the previous iteration. The new conductivity line 84(i) is again determined by interpolating between the conductivity lines measured for the reference materials.

Any number of interpolation routines can be used to determine the conductivity value $C_i$ and corresponding conductivity line 84(i), based upon the values measured for the reference materials. The preferred embodiment uses a cubic spline interpolation. This interpolation fits a piecewise cubic function to the desired parameters. A cubic spline interpolation gives a smooth, continuous overall fit that can provide a good approximation of a function if there are enough points known for the function. In the preferred embodiment, nineteen reference materials are tested with and without lift-off. The more reference materials used provides more accuracy to the cubic spline interpolation.

Steps 160–190 are repeated until the distance by which the line 84(i) misses the value 90(R, X) is less than the desired tolerance. The final conductivity value $C_i$ is then indicated as the conductivity value of the test material and is output in step 200.

The method of the present invention produces a highly accurate conductivity value through the use of an inexpensive and easy to use apparatus 10. Conductivity is measured through the use of a single measurement for each test material. Using the invention, conductivity measurements can be made with a resolution of approximately 0.02% of the true conductivity value. This is an improvement of two to three times the accuracy of the prior art. Furthermore, the present invention allows conductivity measurements to be easily automated, thus reducing human errors. The method of the present invention could easily be placed within a robotic test system in a production facility. This would allow parts to be automatically inspected for quality control.

Some prior art methods to reduce the influence of lift-off compensate for the influence of lift-off on only the phase of the measured impedance. These systems have built in inaccuracies due to the fact that lift-off changes both the magnitude and phase of the measured impedance. The present invention accounts for the influence of lift-off on both the magnitude and phase of the measured impedance, thus achieving greater accuracy than the prior-art.

In addition to lift-off and conductivity, the frequency of the AC signal driving the probe 20 also affects the measured impedance. Increasing the frequency causes the measured conductivity points 50 (FIG. 2) to move clockwise around the curve 50. Proper frequency adjustment can be used to place the operating area of apparatus 10 on the lower region of the curve 50. In this region, the conductivity curve is relatively horizontal and the impedance changes due to the material's conductivity can be easily distinguished from the impedance changes caused by lift-off. Therefore, it is desirable to use a lower frequency signal to drive probe 20 when materials of higher conductivity values are tested.

While the preferred embodiment of the invention has been illustrated and described, it will be appreciated that various changes can be made therein without departing from the spirit and scope of the invention. As an example, the preferred invention uses a single probe 20 to both induce an eddy-current and to measure the eddy-current induced in the test material. Alternate embodiments could use two separate probes or two separate windings mounted on the same probe. In such a case, one probe or winding would be used to generate the magnetic field and the other probe or winding would be used to detect the eddy-current's amplitude and phase.

The embodiments of the invention in which an exclusive property or privilege is claimed are defined as follows:

1. A method for reducing the influence of probe lift-off on eddy-current conductivity measurements, the method comprising the steps of:
   (a) using an eddy-current probe, making at least two conductivity measurements for each of a plurality of reference materials, each reference material having a different value of conductivity, to produce calibration data, wherein the two conductivity measurements made on each reference material are made at a different amount of lift-off,
   (b) using said probe to make a conductivity measurement for a test material; and
   (c) digitally adjusting the conductivity measurement for the test material by digitally interpolating between the calibration data to take into account a nonlinear relationship among a measured probe impedance, a material conductivity, and said probe lift-off, to produce a conductivity value for the test material having a reduced dependence on the lift-off of the probe when the conductivity of the test material was measured.

2. The method of claim 1, wherein the conductivity measurement for the test material is made at a single position of the probe with respect to the test material.

3. The method of claim 1, wherein the adjusting step further comprises adjusting the conductivity measurement for the test material for both a phase change and an amplitude change caused by lift-off of the probe when the conductivity of the test material was measured.

4. The method of claim 1, wherein the adjusting step further comprises calculating a quantity representative of the effects of lift-off on a selected value of conductivity using the calibration data.

5. The method of claim 4, wherein the quantity representative of lift-off is a rate of change of reactance with respect to a change in resistance and the adjusting step further comprises determining a difference between the conductivity measurement for the test material and the selected value of conductivity, and iteratively adjusting the selected value of conductivity until the difference is less than a tolerance value.

6. An eddy-current apparatus for measuring the conductivity of the conductive test material and for reducing the influence of probe lift-off on conductivity measurements, the apparatus comprising:
   (a) probe means for inducing an eddy-current in a conductive material;
   (b) detecting means for making a conductivity measurement for a conductive material by utilizing the probe means to induce an eddy-current in the conductive material and detecting the resulting impedance of the probe means; and
   (c) digital processing means comprising:
      (i) calibration means for producing calibration data by making at least two conductivity measurements for each of a plurality of reference materials using the probe means and the detecting means, wherein each reference material has a different value of conductivity and, the two conductivity measurements made on each reference material are made at different amounts of lift-off; and (ii) measurement means for making a conductivity measurement for a test material using the probe means and detecting means, and for adjusting the conductivity measurement for the test material by digitally interpolating between the calibration data to take into account a nonlinear relationship among a measured probe impedance, a material conductivity and said probe lift-off, to produce a conductivity value for the test material having a reduced dependence on the lift-off of the probe means when the conductivity of the test material was measured.

7. The apparatus of claim 6, wherein the measurement means further comprises means for adjusting the conductivity measurement for the test material for both a phase change and an amplitude change caused by lift-off of the probe means when the conductivity of the test material was measured.

8. The apparatus of claim 6, wherein the measurement means further comprises means for calculating a quantity representative of the effects of lift-off on a selected value of conductivity using the calibration data.

9. The apparatus of claim 8, wherein the quantity representative of the effects of liftoff is a rate of change of reactance with respect to a change in resistance.

10. The apparatus of claim 9, wherein the measurement means further comprises means for determining a difference between the selected value of conductivity and the conductivity measurement for the test material, and means for iteratively adjusting the selected value of conductivity until the difference is less than a tolerance value.

11. The apparatus of claim 6, wherein one of the conductivity measurements for each of the plurality of reference materials includes a minimal amount of lift-off.

12. The apparatus of claim 6, wherein the means for making a conductivity measurement further comprises an LCR meter.

* * * * *